(12) United States Patent
Liberman et al.

(10) Patent No.: US 11,395,606 B2
(45) Date of Patent: Jul. 26, 2022

(54) DETECTING HIDDEN HEARING LOSS

(71) Applicant: Massachusetts Eye and Ear Infirmary, Boston, MA (US)

(72) Inventors: M. Charles Liberman, Milton, MA (US); Stephane Maison, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 1005 days.

(21) Appl. No.: 16/071,372

(22) PCT Filed: Jan. 20, 2017

(86) PCT No.: PCT/US2017/014244
§ 371 (c)(1),
(2) Date: Jul. 19, 2018

(87) PCT Pub. No.: WO2017/127619
PCT Pub. Date: Jul. 27, 2017

(65) Prior Publication Data
US 2021/0186380 A1 Jun. 24, 2021

Related U.S. Application Data

(60) Provisional application No. 62/286,233, filed on Jan. 22, 2016.

(51) Int. Cl.
*A61B 5/12* (2006.01)
*A61B 5/00* (2006.01)
(52) U.S. Cl.
CPC ............ *A61B 5/126* (2013.01); *A61B 5/4836* (2013.01)

(58) Field of Classification Search
CPC ........ A61K 38/185; A61P 27/16; A61P 25/00; A61B 5/125; A61B 5/126; A61B 5/4836
See application file for complete search history.

(56) References Cited

U.S. PATENT DOCUMENTS

2002/0176859 A1    11/2002  Gao
2013/0030321 A1*   1/2013   Zhang .................. A61B 5/6815
                                                        600/559

OTHER PUBLICATIONS

Liberman et al., "Dynamics of cochlear synaptopathy after acoustic overexposure," Journal of the Association for Research in Otolaryngology. Apr. 2015. 16: 206-209 (Year: 2015).*
Sergeyenko et al., "Age-Related Cochlear Synaptopathy: An Early-Onset Contributor to Auditory Functional Decline," The Journal of Neuroscience, Aug. 2013, 33: 13686-13694 (Year: 2013).*
International Preliminary Report on Patentability in International Application No. PCT/US2017/014244, dated Aug. 2, 2018.
International Search Report and Written Opinion in Application No. PCT/US17/14244, dated Apr. 7, 2017, 16 pages.
Attias et al., "Detection and Clinical Diagnosis of Noise-Induced Hearing Loss by Otoacoustic Emissions," Noise Health, Jul. 2001, 3(12):19-31.

(Continued)

*Primary Examiner* — Christine H Matthews
*Assistant Examiner* — Joshua Daryl D Lannu
(74) *Attorney, Agent, or Firm* — Fish & Richardson P.C.

(57) ABSTRACT

Non-invasive methods of detecting hidden hearing loss (cochlear synaptopathy) based on detection of an abnormal ratio of Summating Potential (SP)/Action Potential (AP) (SP/AP) Ratios.

10 Claims, 3 Drawing Sheets

(56) References Cited

OTHER PUBLICATIONS

Bauch and Olsen, "Comparison of ABR amplitudes with TIPtrode and mastoid electrodes," Ear Hear, Dec. 1990, 11(6):463-467.

Buran et al., "Onset Coding is Degraded in Auditory Nerve Fibers from Mutant Mice Lacking Synaptic Ribbons," J Neuroscience, Jun. 2010, 30(22): 7587-7597.

Dalgic et al., "Analysis of Vestibular Evoked Myogenic Potentials and Electrocochleography in Noise Induced Hearing Loss," J Int Adv Otol, Aug. 2015, 11(2):127-132.

Ferraro and Durrant, "Electrocochleography in the evaluation of patients with Ménière's disease/endolymphatic hydrops," J Am Acad Audiol, Jan. 2006, 17(1): 45-68.

Gao, "Therapeutic potential of neurotrophins for treatment of hearing loss," Mol Neurobiol. Winter 1998, 17(1-3): 17-31.

Gillespie and Shepherd, "Clinical application of neurotrophic factors: the potential for primary auditory neuron protection," Eur J Neurosci, Nov. 2005, 22(9): 2123-2133.

Glattke and Robinette, Otoacoustic emission. In: Roeser R, Valente M, editors. AUDIOLOGY, 3-vol. Set: Diagnosis, Treatment and Practice Management. 2nd ed. New York: Thieme New York; 2007.

Henning and Bobholz, "Distortion product otoacoustic emissions in college music majors and nonmusic majors," Noise Health, Jan.-Feb. 2016, 18(80): 10-20.

Killion et al., "Development of a quick speech-in-noise test for measuring signal-to-noise ratio loss in normal-hearing and hearing-impaired listeners," J Acoust Soc Am, Oct. 2004, 116: 2395-2405.

Kim et al., "Electrocochleography is more sensitive than distortion-product otoacoustic emission test for detecting noise-induced temporary threshold shift," Otolaryngol Head Neck Surg, Oct. 2005, 133(4): 619-624.

Liberman et al., "Dynamics of cochlear synaptopathy after acoustic overexposure," Journal of the Association for Research in Otolaryngology, Apr. 2015, 16: 206-209.

Liberman et al., "Toward a Differential Diagnosis of Hidden Hearing Loss in Humans," PLOS One, Sep. 11, 2016.

Nam and Won, "Extratympanic electrocochleographic changes on noise-induced temporary threshold shift," Otolaryngol Head Neck Surg, Apr. 2004, 130(4): 437-442.

Nilsson et al., "Development of the Hearing in Noise Test for the measurement of speech reception thresholds in quiet and in noise," J Acoust Soc Am, Feb. 1994, 95(2): 1085-99.

QuickSIN Speech-in-Noise Test, "Version 1.3 [compact disc]," Elk Grove Village, Ill: Etymotic Research, 2001.

Santarelli et al., "Neural and receptor cochlear potentials obtained by transtympanic electrocochleography inauditory neuropathy," Clin Neurophysiol, May 2008, 119(5): 1028-1041.

Sergeyenko et al., "Age-Related Cochlear Synaptopathy: An Early-Onset Contributor to Auditory Functional Decline," The Journal of Neuroscience, Aug. 2013, 33: 13686-13694.

Shaheen et al., "Towards a Diagnosis of Cochlear Neuropathy with Envelope Following Responses," J Assoc Res Otolaryngol, Dec. 2015, 16(6): 727-745.

Wan et al., "Neurotrophin-3 regulates ribbon synapse density in the cochlea and induces synapse regeneration after acoustic trauma," ELife, Oct. 2014, e03564.

Wilson and Burks, "Use of 35 words for evaluation of hearing loss in signal-to-babble ratio: A clinic protocol," J Rehabil Res Dev, Nov.-Dec. 2005, 42(6): 839-852.

Wilson, "Development of a speech-in-multitalker-babble paradigm to assess word-recognition performance," J Am Acad Audiol, Nov. 2003, 14(9): 453-470.

Yuan et al., "Ouabain-Induced Cochlear Nerve Degeneration: Synaptic Loss and Plasticity in a Mouse Model of Auditory Neuropathy," JARO, Feb. 2014, 15(1): 31-43.

* cited by examiner

DETECTING HIDDEN HEARING LOSS

CLAIM OF PRIORITY

This application is a 371 U.S. National Phase Application of PCT/US2017/014244, filed on Jan. 20, 2017, which claims the benefit of U.S. Provisional Patent Application Ser. No. 62/286,233, filed on Jan. 22, 2016. The entire contents of the foregoing are hereby incorporated by reference.

FEDERALLY SPONSORED RESEARCH OR DEVELOPMENT

This invention was made with Government support under Grant No. DC000188 awarded by the National Institutes of Health. The Government has certain rights in the invention.

TECHNICAL FIELD

Described herein are non-invasive methods of detecting hidden hearing loss (cochlear synaptopathy) based on detection of an abnormal ratio of Summating Potential (SP)/Action Potential (AP) (SP/AP) Ratios.

BACKGROUND

To date, hearing aids are the only available therapeutic treatment for hearing loss, and while the issue of audibility can be successfully addressed, gain in intelligibility is often experienced as poor, particularly in noisy environments. Several dysfunctions have been identified as causes for hearing loss including missing cells of the auditory nerve, the chief manifestation of which is a loss in speech discrimination, particularly in conditions of background noise and high-reverberation environments. This condition is known as cochlear neuropathy.

SUMMARY

Provided herein are methods for detecting cochlear synaptopathy (hidden hearing loss) in a subject, e.g., a subject with a normal audiogram response. The methods include obtaining a auditory brainstem recording using a first electrode placed on the forehead of the subject, and a second electrode placed in the ear canal of the subject; determining an amplitude of a Summating Potential (SP) and an Action Potential (AP) in response to 100 is clicks of alternating polarity, at 94.5 dBnHL and 9.1 Hz; determining a ratio of SP to AP; and comparing the SP/AP ratio to a reference ratio, wherein an SP/AP ratio above the reference ratio indicates that the subject has cochlear synaptopathy (hidden hearing loss).

In some embodiments, the method comprises performing threshold audiometry, e.g., pure tone audiometry (PTA), and the subject has a normal audiogram response, i.e., has thresholds below 20 db or 25 db Hearing Level (HL) at 250-8000 hz for PTA In some embodiments, the method comprises performing High Frequency Audiometry (HFA), and the subject has thresholds of 10-20 db at from 8,000-16,000 Hz. In some embodiments, the method comprises performing one or more of tympanometry, otoacoustics emission testing (e.g., Distortion Product Otoacoustic Emissions (DPOAE)), and speech audiometry, and the subject has normal hearing based on those tests. In some embodiments, the method comprises performing Hearing-in-Noise Test (HINT) or Speech in Noise (SIN)), and the subject has impaired hearing based on those tests.

In some embodiments, the methods include selecting the subject for treatment with a neurotrophin. In some embodiments, the methods include treating the subject with a neurotrophin. In some embodiments, the neurotrophin is nerve growth factor (NGF), brain-derived neurotrophic factor (BDNF), neurotrophin-3 (NT-3) and/or neurotrophin-4/5 (NT-4/5). In some embodiments, the neurotrophin is administered locally to the ear of the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
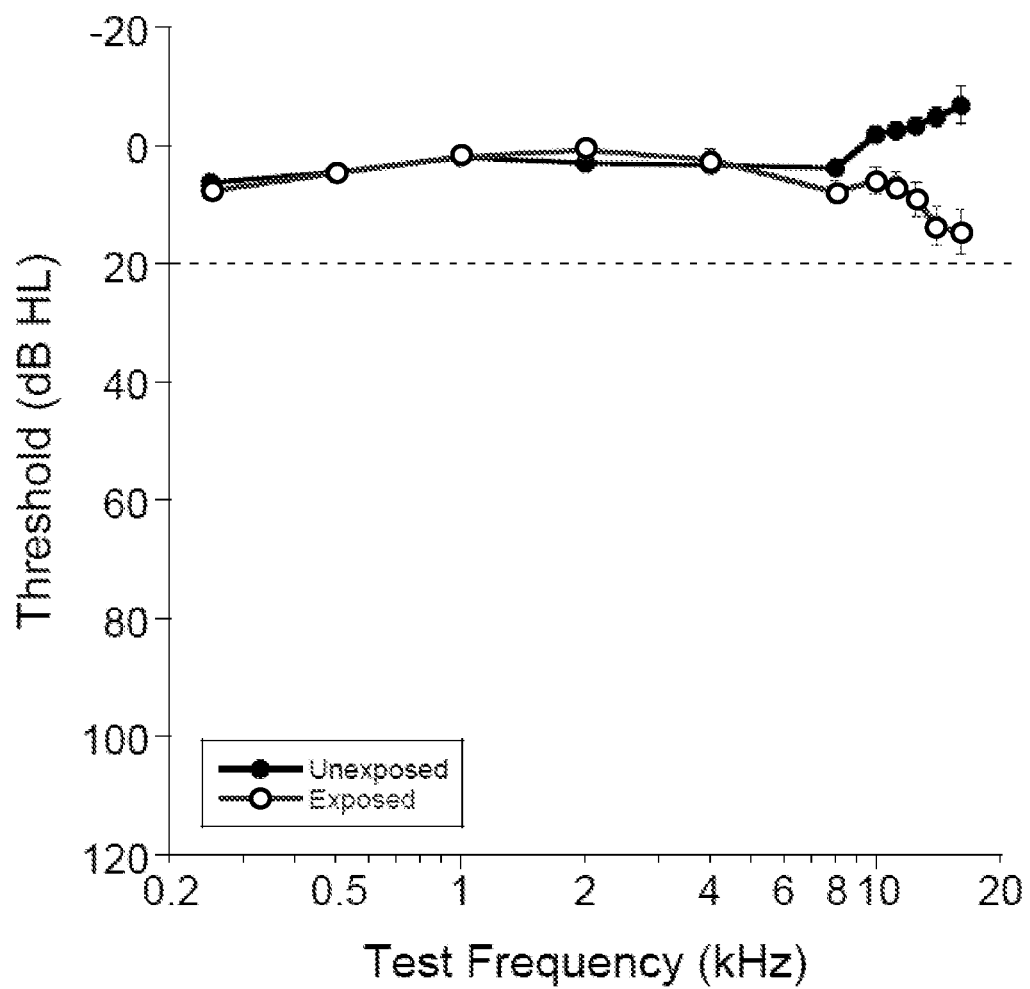
FIG. 1. This audiogram shows the mean hearing sensitivity of unexposed (black) and exposed (red) subjects enrolled in this study. It shows that they can detect pure tones (sounds delivered at one particular pitch) from 250 Hz to 16,000 Hz at levels below 20 dB HL. Thresholds are considered normal if they are below 20 dB HL from 250 Hz to 8000 Hz.

Hearing Loss has been historically assessed through the measurement of auditory thresholds, a method that fails to identify cochlear neuropathy particularly in its earlier stages and at this time, there is no clinical test available to assess the early progression of cochlear neuropathy in patients presenting normal audiometric thresholds.

Described herein are ways to diagnose and monitor this type of "hidden hearing loss" and its resulting loss in intelligibility, as it has obvious public health significance given the reports of increasing hearing loss prevalence earlier in life. Recent research shows that early noise exposure renders the inner ear significantly more vulnerable to aging with deleterious effects on the nature and progression of age-related hearing loss. It is therefore key to implement a method to reveal cochlear neuropathy as hearing conservation programs mandated by law recommend exposure limits that dangerously exceed noise levels that could be contributing to hidden hearing loss.

The ABR is measured by presenting a click (sound stimulus at a single frequency) to a subject, and then measuring the electrophysiological response in that subject using surface electrodes. Measured with an electrode placed in the ear, wave 1 of the ABR resolves into two overlapping waves, the SP component, which is contributed by sensory hair cells, and the AP component, which is reflective of functional neural connections between sensory hair cells and the brain. Previous work showed that reduced amplitude of the AP component corresponds to cochlear synaptopathy, when sound transmission from the ear to the sensory hair cells is intact. Measuring cochlear synaptopathy may become important because cochlear synaptopathy may underlie many different kinds of hearing loss, including age-related and noise-induced hearing loss.

Currently, pure tone audiometry (PTA) is the dominant diagnostic for hearing loss. However, it is a tool ill-suited for measuring cochlear synaptopathy because hearing measured by PTA recovers after trauma even as synaptic deficiencies persist. With the development of new treatments for hearing loss, there will be a need for diagnostics that provide more information about the physiological defects associated with hearing loss, so as to match the appropriate treatment for each subject depending on the cause of their deficit. For example, are synapses intact? Are hair cells intact? Have neuronal axons degenerated and to what extent? The present methods can be used to identify and select subjects who have hidden hearing loss and optionally treat them, e.g., using neurotrophins to reverse synaptopathy. In some embodiments of the present methods, the SP/AP ratio is measured in combination with other hearing assays to detect hidden hearing loss, e.g., in combination with Pure Tone Audiometry (PTA) and High Frequency Audiometry (HFA), Word recognition in different conditions, and/or Distortion Product Otoacoustic Emissions (DPOAEs/Otoacoustic Emissions. A subject who has within normal-range results on one or more of these tests, but who has an abnormally elevated SP/AP ratio, can be diagnosed with HHL/cochlear synaptopathy.

Summating Potential (SP)/Action Potential (AP) (SP/AP) Ratios

Sergeyenko et al., The Journal of Neuroscience, 33(34): 13686-13694 (2013), describes studies in mice and indicates on page 13692, second column, third paragraph that wave 1 might be useful in diagnosing cochlear synaptopathy. However, there are limitations to the usefulness of wave 1 outside of the laboratory as it can vary depending on the tester and also depending on the variability of the human head. The present invention is based on experiments in human subjects which indicate that hidden hearing loss associated with noise exposure can be discriminated in humans using the SP/AP ratio.

Figure 2:
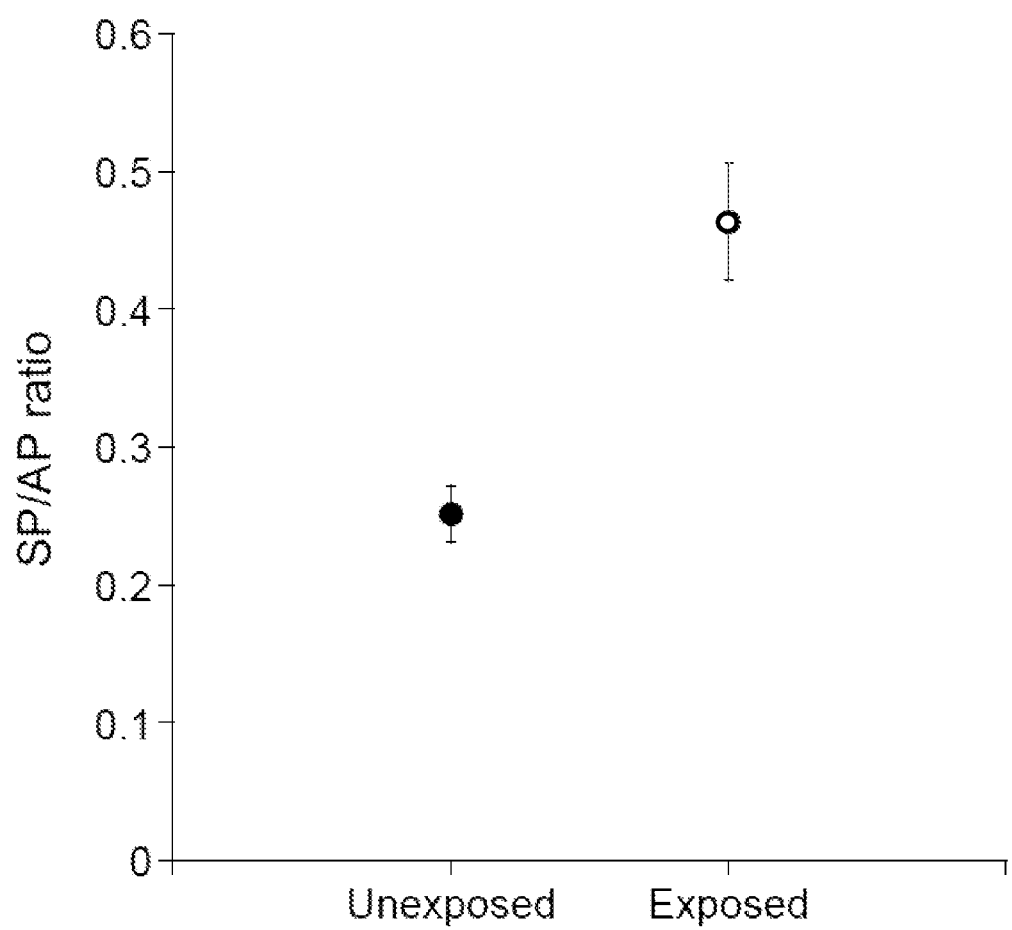
FIG. 2. These waveforms represent the electrical potentials recorded from the scalp and ears of subjects in response to an acoustic stimulus. They show different peaks and troughs that represent different generators (or source of potential). The AP (Action Potential) also known as Wave 1 when recording ABR (Auditory Brainstem Responses) represents the activity of the auditory nerve. The SP (Summating Potential) is thought to reflect what's going on with the sensory cells in the inner ear. This graph shows that in exposed subjects, the AP amplitude on average is reduced and the SP amplitude is enhanced. The SP/AP ratio is therefore enhanced in exposed subjects.
Figure 3:
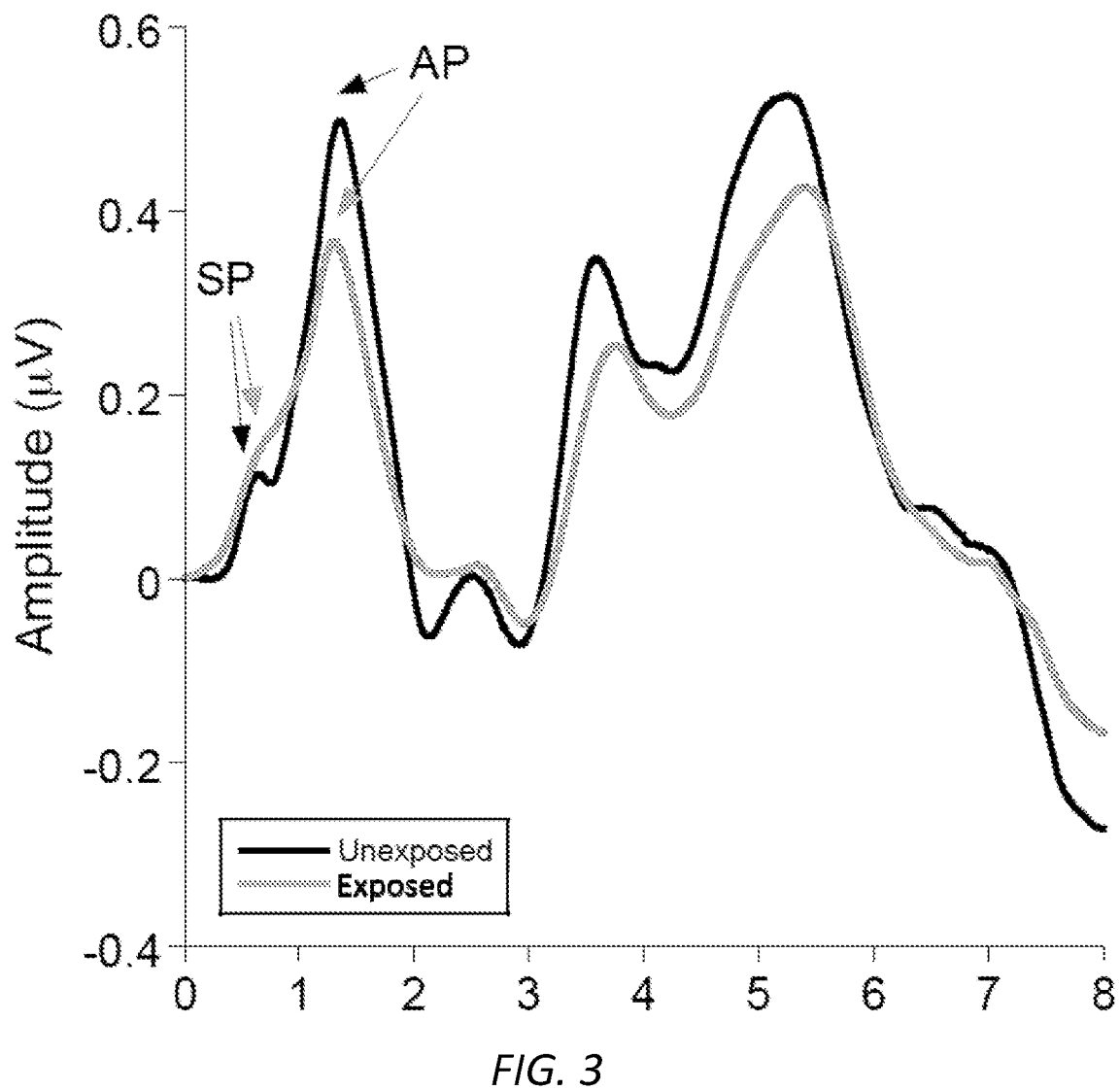
FIG. 3. A line graph reflecting the difference in SP/AP ratio between the two groups of subjects.

The action potential, or AP, is the summed response of the synchronous firing of the nerve fibers; the first and largest wave of the AP is identical to wave 1 of the auditory brainstem response (ABR). The SP is a plateau just before wave 1 (the AP) in ABRs (see, e.g., the arrow in FIG. 2C of Buran et al., Journal of Neuroscience, 30(22):7587-7597 (2010)). In mice treated with a drug, ouabain, that selectively destroys neurons while keeping the hair cells intact, the SP remained unchanged after total loss of cochlear neurons (Yuan et al., JARO 15: 31-43 (2014), FIG. 1). As noted in Sergenyenko et al. Journal of Neuroscience, 33(34): 13686-13694 (2013) (see, e.g., FIG. 2), as cochlear synaptopathy sets in in aging mice, AP goes down and SP stays the same. Lastly, when oaubain was used acutely to remove the auditory nerve (AN) contributions to potentials, the AP slowly declined while the SP stayed (see Shaheen et al., J Assoc Res Otolaryngol. 2015 December; 16(6):727-45). All of this was consistent with the idea that SP, the shoulder on the rising phase of Wave 1 in ABR recordings, is generated by hair cells, and that its amplitude is unaffected when the cochlear neurons are selectively affected.

The SP/AP ratio has been used in the diagnosis of Meniere's disease/endolymphatic hydrops in humans (see Ferraro and Durrant, J Am Acad Audiol. 2006 January; 17(1):45-68). Also in humans, abnormal SP/AP ratios have been described in noise-exposed ears (Nam and Won, Otolaryngol Head Neck Surg. 2004 April; 130(4):437-42; Kim et al., Otolaryngol Head Neck Surg. 2005 October; 133(4): 619-24; Dalgic et al., J Int Adv Otol. 2015 August; 11(2): 127-3) and used to identify hair cell vs. neural involvement in cases of auditory neuropathy (see, e.g., Santarelli et al., Clin Neurophysiol. 2008 May; 119(5):1028-41). However, the use of changes in SP/AP in human ears with normal thresholds to non-invasively detect 'hidden hearing loss' or cochlear synaptopathy has not been previously described. The present methods are also valuable as an assay of treatment effects designed to reconnect hair cells and auditory nerve fibers.

In some embodiments, to measure SP/AP in humans, an atypical configuration of electrodes is used, with one external (preferably attached to the subject's forehead or scalp), and ear canal-inserted electrodes, e.g., TIPTRODES, which are typically electrode inserts covered with gold foam for insertion in the ear canal (see, e.g., Bauch and Olsen, Ear Hear. 1990 December; 11(6):463-7). These internal electrodes are somewhat similar to earbud headphones in that they deliver sounds within the ear canal, but these record sounds as well within the ear canal. In some embodiments of the present methods, no electrodes are placed on the earlobe. Prior to insertion of the in-ear electrode, the ear canal must be cleaned. For example, the visible portion of the ear canal can be cleaned by using a cotton swab, e.g., dipped or coated in a cleanser suitable for electrophysiology such as Nuprep® exfoliant gel. A conductive gel, e.g., Spectra® 360 electrode gel, is then applied on the same portion and over the gold foil of each tiptrode before insertion.

Pure Tone Audiometry (PTA) and High Frequency Audiometry (HFA)

Conventional PTA can be performed for each subject in an art-accepted acoustic chamber at the following frequencies: 250, 500, 1000, 2000, 3000, 4000, 6000, and 8000 Hz (see, e.g., American National Standard Specification for Audiometers. New York: Acoustical Society of America; 1996). HFA can also be performed with the same devices at 10000, 12000, 14000, and 16000 Hz. Methods and devices for performing both PTA and HFA are well known in the art; see, e.g., Mehrparvar et al., Noise Health. 2011 November-December; 13(55):402-6; American National Standard Specification for Audiometers. New York: Acoustical Society of America; 1996; Guidelines for manual pure-tone threshold audiometry.: American Speech-Language-Hearing Association; 2005. Available from asha.org/policy.

Word Recognition in Different Conditions,

In some embodiments, word recognition is tested under different conditions, e.g., using speech audiometry, e.g., speech reception threshold (SRT) testing, word recognition score (WRS), Hearing in Noise Test (HINT), Words in Noise (WIN), QuickSIN, Bamford-Kowal-Bench SIN (BKB-SIN). See, e.g., Nilsson et al., J Acoust Soc Am. 1994; 95(2):1085-99; Wilson et al., J Am Acad Audiol. 2003; 14(9):453-470; Wilson and Burks J Rehabil Res Dev. 2005; 42(6):839-852; QuickSIN Speech-in-Noise Test, Version 1.3 [compact disc]. Elk Grove Village, Ill.: Etymotic Research; 2001. Killion et al., J Acoust Soc Am. 2004; 116:2395-2405.

Distortion Product Otoacoustic Emissions (DPOAEs/Otoacoustic Emissions

In the United States, otoacoustic emissions are the basis of a simple, non-invasive, test for hearing defects in newborn babies and in children who are too young to cooperate in conventional hearing tests. They can also be used to assist in differential diagnosis of inner ear vs. higher level hearing losses (such as cochlear neuropathy; see, e.g., Henning and Bobholz, Noise Health. 2016 January-February; 18(80):10-20). The internal electrodes used to measure SP/AP can also be used as otoacoustic emission probes. Methods and devices for use in measuring OAE or DPOAE are known in the art; see, e.g., Glattke and Robinette, Oloacustie emission. In: Roeser R, Valente M, editors. AUDIOLOGY, 3-Volume Set: Diagnosis, Treatment and Practice Management. 2nd ed. New York: Thieme New York: 2007; Attias et al., Noise Health. 2001; 3(12):19-31; Henning and Bobholz, Noise Health. 2016 January-February; 18(80):10-20.

Methods of Treatment

Once identified by a method described herein as having hidden hearing loss, a subject can be selected for treatment with and optionally administered a neurotrophin, e.g., nerve growth factor (NGF), brain-derived neurotrophic factor (BDNF), neurotrophin-3 (NT-3) and/or neurotrophin-4/5 (NT-4/5). See, e.g., US20020176859; Gillespie and Shepherd, Eur J Neurosci. 2005 November; 22(9): 2123-2133; Gao, Mol Neurobiol. 1998 Winter; 17(1-3):17-31; Wan et al., eLife 2014; 10.7554/eLife.03564. The methods can include administering the neurotrophin protein, an agonist, a nucleic acid encoding the protein, or an agent that increases expression of the neurotrophin. Alternatively, a hearing aid can be used.

EXAMPLES

The invention is further described in the following examples, which do not limit the scope of the invention described in the claims.

Example 1. Hidden Hearing Loss in Young Adults: Audiometry, Speech Discrimination and Electrophysiology Most research on noise-induced or age-related hearing loss has focused on threshold elevation and the loss of sensory cells that typically causes it. Recent animal work suggests that synapses between hair cells and cochlear nerve terminals are the most vulnerable elements of the inner ear (Kujawa and Liberman, 2015). We hypothesize that acoustic overexposure in humans causes cochlear neuropathy before it elevates audiometric thresholds and that electrophysiological recordings that allow comparison of the hair-cell summating potential (SP) to auditory nerve action potential (AP) could be a useful diagnostic.

To test this, we recruited college age subjects, aged 18-30, with "normal hearing". Subjects included those reporting minimal exposure to loud music and others (from a local music school) who were exposed regularly without hearing protection.

Otoscopic Examination and Hearing Evaluation

In order to confirm normal hearing and ear health, the participants first had a conventional audiometric evaluation in a test booth at the Northeastern University Speech-Language and Hearing Center on the 5th floor of the Behrakis Health Sciences building. The evaluation included a) an otoscopic examination of the ear canal to confirm absence of impacted ear wax, b) tympanometry to make sure the subject's ear drum is mobile and that the subject is not suspected of having any middle ear pathology that could interfere with hearing, and c) threshold responses to pure tones presented via air conduction through standard audiometric earphones at several frequencies to confirm that the subject's hearing is within normal limits. For this third part of the evaluation, the subject raised his/her hand whenever he or she heard a tone. If the subject was found to have hearing outside of normal limits or is suspected of having outer or middle ear pathology, he or she was counseled to follow up with an otolaryngologist, but was excluded from the study. Cochlear function was assessed by threshold audiometry (250 Hz-16,000 Hz), DPOAEs (L2=55 dB SPL, L1=65 dB SPL, f2 varied from 500 Hz to 12,000 Hz) and ABRs recorded from Tiptrodes in response to 100 µs clicks of alternating polarity, at 94.5 dBnHL and 9.1 Hz. NU-6 word recognition scores were assessed at 35 dB HL in absence or presence of noise at 5 and 0 dB SNR, as well as on two time-compressed NU-6 word lists (45% or 65% compression with 0.3 sec reverberation)

All subjects had similar, and normal, audiometric thresholds (<20 dB HL) from 250 Hz to 8,000 Hz; however, high-exposure subjects had poorer thresholds (10 to 20 dB) from 8,000-16,000 Hz. DPOAEs were not significantly different between groups. While absolute and inter-peak latencies of all ABR waves were normal and similar across groups, a significant increase in the SP/AP ratio was observed in high-exposure vs. low-exposure subjects (0.25±0.02 vs. 0.43±0.03, respectively). No difference in performance for word recognition in noise was observed between groups, however the high-exposure subjects performed significantly worse on the 45% time-compressed NU-6 word list with reverberation.

The electrophysiological results were consistent with a selective loss of cochlear-nerve fibers in the high-exposure group and suggested that SP/AP ratios are useful in early detection. Poorer performance in word recognition under challenging conditions also suggested that primary neural degeneration is a key contributor to hearing impairments in those with sensorineural hearing loss.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting cochlear synaptopathy in a subject, the method comprising:
obtaining an auditory brainstem recording using a first electrode placed on a forehead of the subject, and a second electrode placed in an ear canal of the subject;
determining an amplitude of a Summating Potential (SP) and an Action Potential (AP) in response to 100 µs clicks of alternating polarity, at 94.5 dBnHL and 9.1 Hz;

determining a ratio of the SP to AP;
comparing the SP/AP ratio to a reference ratio;
determining a subject who has an SP/AP ratio above the reference ratio as having cochlear synaptopathy; and
treating the subject who is determined as having cochlear synaptopathy with a neurotrophin.

2. The method of claim 1, wherein the method further comprises performing threshold audiometry, and determining the subject has a normal audiogram response.

3. The method of claim 2, wherein the threshold audiometry is pure tone
audiometry (PTA), and the subject has thresholds below 25 db Hearing Level (HL) at 250-8000 Hz.

4. The method of claim 3, wherein the subject has thresholds below 20 db Hearing Level (HL) at 250-8000 Hz.

5. The method of claim 2, wherein the method comprises performing High Frequency Audiometry (HFA), and the subject has thresholds of 10-20 db at from 8,000-16,000 Hz.

6. The method of claim 1, wherein the method further comprises performing one or more of tympanometry, otoacoustics emission testing, and speech audiometry, and determining subject has normal hearing based on one or more of the tympanometry, otoacoustics emission testing, and speech audiometry.

7. The method of claim 6, wherein the otoacoustics emission testing comprises testing Distortion Product Otoacoustic Emissions (DPOAE).

8. The method of claim 1, wherein the method further comprises performing Hearing-in-Noise Test (HINT) or Speech in Noise (SIN), and determining the subject has impaired hearing based on either of the Hearing-in-Noise (HINT) or Speech in Noise (SIN).

9. The method of claim 1, wherein the neurotrophin is neurotrophin-3 (NT-3), nerve growth factor (NGF), brain-derived neurotrophic factor (BDNF), and/or neurotrophin-4/5 (NT-4/5).

10. The method of claim 1, wherein the neurotrophin is administered locally to an ear of the subject.

* * * * *